US010869967B2

(12) United States Patent
Schleicher et al.

(10) Patent No.: US 10,869,967 B2
(45) Date of Patent: Dec. 22, 2020

(54) RIGID SENSOR STOPPER FOR USE IN DRUG DELIVERY DEVICES

(71) Applicant: Verily Life Sciences LLC, Mountain View, CA (US)

(72) Inventors: Brett Schleicher, San Francisco, CA (US); Chuangang Lin, Fremont, CA (US); James Etzkorn, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 247 days.

(21) Appl. No.: 15/862,375

(22) Filed: Jan. 4, 2018

(65) Prior Publication Data

US 2018/0193567 A1 Jul. 12, 2018

Related U.S. Application Data

(60) Provisional application No. 62/443,493, filed on Jan. 6, 2017.

(51) Int. Cl.
*A61M 5/315* (2006.01)
*A61M 5/34* (2006.01)
(Continued)

(52) U.S. Cl.
CPC ...... *A61M 5/31565* (2013.01); *A61M 5/1684* (2013.01); *A61M 5/31511* (2013.01);
(Continued)

(58) Field of Classification Search
CPC .. A61M 2205/3327; A61M 2205/3375; A61M 2205/3576; A61M 2205/50;
(Continued)

(56) References Cited

U.S. PATENT DOCUMENTS 4,358,839 A 11/1982 Wittke
5,311,871 A * 5/1994 Yock .................... A61B 8/0833
600/461

(Continued)

FOREIGN PATENT DOCUMENTS

WO 2010/133676 A1 11/2010
WO 2011/032956 A2 3/2011
(Continued)

OTHER PUBLICATIONS

International Search Report and Written Opinion dated May 14, 2018 from the International Searching Authority for International Application No. PCT/US2018/012626, filed Jan. 5, 2018, 13 pages.
(Continued)

*Primary Examiner* — Quynh-Nhu H. Vu
(74) *Attorney, Agent, or Firm* — Christensen O'Connor Johnson Kindness PLLC (57) ABSTRACT

The present disclosure relates to a rigid sensor stopper adapted for use in a drug delivery device. In one implementation, a rigid sensor stopper may include a transducer, a power source, a rigid molding or casing, and at least one elastomeric seal. The molding may be formed from over-molding or insert molding, and the casing may be formed from injection molding, machining, or forged casing. The at least one elastomeric seal may include at least two o-rings.

17 Claims, 8 Drawing Sheets

(51) Int. Cl.
*A61M 5/168* (2006.01)
*A61M 5/24* (2006.01)

(52) U.S. Cl.
CPC .... *A61M 5/31525* (2013.01); *A61M 5/31568* (2013.01); *A61M 5/344* (2013.01); *A61M 5/24* (2013.01); *A61M 2205/3327* (2013.01); *A61M 2205/3375* (2013.01); *A61M 2205/3576* (2013.01); *A61M 2205/50* (2013.01); *A61M 2205/8206* (2013.01)

(58) Field of Classification Search
CPC ........ A61M 2205/8206; A61M 5/1684; A61M 5/24; A61M 5/31511; A61M 5/31525; A61M 5/31565; A61M 5/31568; A61M 5/344; A61M 5/315; A61M 5/31515; A61M 2005/315
See application file for complete search history.

(56) References Cited

U.S. PATENT DOCUMENTS

| | | | |
|---|---|---|---|
| 5,678,189 | A | 10/1997 | Barnes |
| 5,728,074 | A | 3/1998 | Castellano et al. |
| 5,826,066 | A | 10/1998 | Jardine et al. |
| 6,585,698 | B1 | 7/2003 | Packman et al. |
| 7,927,281 | B2 | 4/2011 | Wheeler |
| 8,226,599 | B2 | 7/2012 | Engle |
| 8,556,866 | B2 | 10/2013 | Krulevitch et al. |
| 8,560,271 | B2 | 10/2013 | Koehler et al. |
| 8,817,258 | B2 | 8/2014 | Whalley et al. |
| 9,008,764 | B2 | 4/2015 | Larsen |
| 9,101,723 | B2 | 8/2015 | Larsen |
| 9,250,111 | B2 | 2/2016 | Whalley et al. |
| 9,255,830 | B2 | 2/2016 | Whalley et al. |
| 9,861,756 | B1 * | 1/2018 | Krasnow ............... G01F 11/027 |
| 10,369,276 | B2 * | 8/2019 | Uber, III ........... A61M 5/14546 |
| 10,413,676 | B1 * | 9/2019 | Krasnow .............. A61B 5/0026 |
| 2005/0209601 | A1 | 9/2005 | Bowman et al. |
| 2008/0188813 | A1 | 8/2008 | Miller et al. |
| 2008/0243088 | A1 | 10/2008 | Evans |
| 2009/0043253 | A1 | 2/2009 | Podaima |
| 2009/0069742 | A1 | 3/2009 | Larsen |
| 2011/0009824 | A1 | 1/2011 | Yodfat et al. |
| 2012/0101451 | A1 | 4/2012 | Boit et al. |
| 2012/0195182 | A1* | 8/2012 | Pommereau ....... A61M 5/31511 369/127 |
| 2012/0302849 | A1 | 11/2012 | Grant et al. |
| 2013/0116666 | A1 | 5/2013 | Shih et al. |
| 2013/0310756 | A1 | 11/2013 | Whalley et al. |
| 2013/0331635 | A1* | 12/2013 | Hoffman ............. A61M 5/1785 600/5 |
| 2014/0249410 | A1* | 9/2014 | Uber, III ............... A61M 5/007 600/432 |
| 2014/0379874 | A1 | 12/2014 | Starr et al. |
| 2015/0112316 | A1 | 4/2015 | Cudak et al. |
| 2015/0174330 | A1* | 6/2015 | Nagel ..................... G01F 17/00 604/218 |
| 2015/0174342 | A1 | 6/2015 | Mitrosky et al. |
| 2015/0209510 | A1 | 7/2015 | Burkholz et al. |
| 2015/0302818 | A1* | 10/2015 | Cowe ..................... B41J 3/4076 604/189 |
| 2016/0030683 | A1 | 2/2016 | Taylor et al. |
| 2016/0074587 | A1 | 3/2016 | Searle et al. |
| 2016/0243311 | A1* | 8/2016 | Fournier ................. A61L 31/10 |
| 2016/0259913 | A1* | 9/2016 | Yu ............................ A61M 5/31 |
| 2017/0043096 | A1* | 2/2017 | Moritz ...................... B08B 3/10 |
| 2017/0312445 | A1* | 11/2017 | Mirov ................. G06F 19/3468 |
| 2018/0008787 | A1* | 1/2018 | Schriver ............. A61M 5/2066 |

FOREIGN PATENT DOCUMENTS

| | | |
|---|---|---|
| WO | 2014/009442 A1 | 1/2014 |
| WO | 2014/145906 A2 | 9/2014 |

OTHER PUBLICATIONS

Aoluguya BC-W10 E-monitoring Smart Vacuum Wine Preserver Stopper w/ Temperature Sensor, Timer, DealExtreme, retrieved Nov. 2, 2016, URL: http://www.dx.com/p/aoluguya-bc-w10-e-monitoring-intelligent-vacuum-wine-preserver-stopper-w-temperature-sensor-timer-364999#.WBosLtUrKUk, 6 pages.

ENFit Compliant NeoConnect Pharmacy Syringes, NeoMed, retrieved Nov. 2, 2016, URL: http://www.neomedinc.com/product/neoconnect-pharmacy-syringes/, 3 pages.

* cited by examiner

RIGID SENSOR STOPPER FOR USE IN DRUG DELIVERY DEVICES

RELATED APPLICATIONS

This application claims priority to provisional application 62/443,493, filed Jan. 6, 2017, which is incorporated by reference in its entirety.

TECHNICAL FIELD

The present disclosure relates generally to the field of drug delivery devices. More specifically, and without limitation, this disclosure relates to a rigid sensor stopper adapted for use in a drug delivery device. The stopper may be used in various drug delivery devices, for example, a syringe, infusion pump, auto injector, or an injection pen.

BACKGROUND

Drug delivery systems, such as syringes and injection pens, generally include stoppers, which create a seal within the cartridge or barrel and allow for the drug to be administered when the displacement mechanism (plunger) is depressed. Traditional stoppers are typically fabricated with an elastomeric rubber material. Elastomeric materials may not be optimal for a drug delivery device with a sensor incorporated into the delivery device and/or drug cartridge because such materials attenuate the measurement signal.

SUMMARY

In view of the foregoing, embodiments of the present disclosure provide a rigid sensor stopper incorporating elastomeric elements. In accordance with some embodiments, a molded assembly or rigid casing is provided for the sensor and other electronics. Due to its rigidity, the assembly or casing reduces attenuation of the measurement signal while remaining compliant with the drug delivery device. In addition, the elastomeric elements can seal the drug cartridge while not interfering with the displacement mechanism.

According to an exemplary embodiment of the present disclosure, a rigid sensor stopper is described. The device may include a transducer, a battery, a rigid molding, and at least one seal. The molding may be formed by overmolding surrounding the transducer (or other sensor elements such as optical, magnetic, and capacitive sensors) and the battery, or insert molding surrounding the transducer and the battery. In one embodiment, the at least one seal may be elastomeric.

According to a yet further exemplary embodiment of the present disclosure, a rigid sensor stopper for use in a drug delivery device is described. The device may include a transducer, a battery, a rigid casing, and at least one seal. The casing may be formed by injection molding, machining, or forged casing. Moreover, the transducer and the battery may be inserted prior to the sealing of the rigid casing, and the at least one seal may be elastomeric. In one embodiment, the rigid casing could also be installed into a cartridge and filled prior to the insertion of electronics.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

— 2 —

It is to be understood that the foregoing general description and the following detailed description are exemplary and explanatory only, and are not restrictive of the disclosed embodiments.

BRIEF DESCRIPTION OF THE DRAWINGS

The accompanying drawings, which comprise a part of this specification, illustrate several embodiments and, together with the description, serve to explain the disclosed principles. In the drawings.

DETAILED DESCRIPTION

The disclosed embodiments relate to a rigid sensor stopper adapted for use in a drug delivery device, as well as a phase-change-material-protected power source. Advantageously, the exemplary embodiments may reduce attenuation of the measurement signal from the sensor while remaining compliant with the drug delivery device. Applications consistent with the present disclosure encompass a syringe, an injection pen, other drug delivery devices, and wearable electronics.

According to an aspect of the present disclosure, a rigid sensor stopper is provided. The stopper may include one or more transducers to detect the position of the stopper in a cartridge or syringe of a drug delivery device (e.g., by sending and receiving ultrasonic signals). The position of the stopper may be used to calculate a volume of fluid dispensed from the cartridge. In some embodiments, the one or more transducers may include an ultrasonic transducer. For example, the one or more transducers may include a PZT transducer. In other embodiments, other sensors may be included such as an acoustic transceiver, a photodiode, an encoder, a hall effect sensor, etc.

According to a further aspect of the present disclosure, the stopper may include one or more power sources. In some embodiments, the one or more power sources may comprise a DC power source and include a battery, a capacitor, etc. In other embodiments, the one or more power sources may comprise an AC power source. In some embodiments, the stopper may be powered by an external power source through an inductive, RF connection, or the like.

According to a further aspect of the present disclosure, the stopper may include one or more additional electronic elements. By way of example, the one or more electronic elements may include a microcontroller, an amplifier, an analog-to-digital converter, etc.

According to a further aspect of the present disclosure, the stopper may include one or more telemeters or transmitters. By way of example, the one or more telemeters/transmitters may include a radio transmitter, an antenna, etc.

Consistent with embodiments of the present disclosure, the stopper may include a rigid molding. In certain aspects, the molding may be formed from overmolding surrounding the sensor, the transducer, the power source, etc. In other aspects, the molding may be formed from insert molding surrounding the transducer, the power source, etc.

In other embodiments, the stopper may include a sealed rigid casing. The transducer, the power source, etc. may be inserted into the casing prior to sealing it. For example, the casing may be sealed using an adhesive, resistance welding, ultrasonic welding, friction welding, laser welding, Interference fit, snap features, additional fastening components, etc. In certain aspects, the casing may be formed from injection molding. In other aspects, the casing may be formed from machining. In still other aspects, the casing may be formed from forged casing.

Consistent with other aspects of the present disclosure, the casing may comprise glass. The casing may be hermetically sealed using flame sealing. In other aspects, the casing may include a cap. The cap may seal the casing after the transducer, the power source, etc., are inserted therein.

In some embodiments, the casing may include potting and/or backfill. Advantageously, this may remove dead space within the casing and secure the transducer, the power source, etc. In some embodiments, the casing may include a getter. Advantageously, this may absorb moisture within the casing that could damage the transducer, the power source, etc. In some embodiments, the casing and the potting may include material whose acoustic resonance matches the frequency of the transducer, for example, a soundboard. Preferably, such material is rigid in order to function as an effective soundboard. Advantageously, this may improve the range of the transducer. In some embodiments, the casing may be optically clear for optical sensors (for light transmission), or magnetically transparent for hall sensors, or insulative.

Consistent with embodiments of the present disclosure, the stopper may include at least one seal. The at least one seal may be elastomeric. In some embodiments, the at least one seal may cover the entirety of the stopper. For example, the at least one seal may be integrated with the molding or casing and may be formed from overmolding or insert molding. In other embodiments, the at least one seal may comprise at least two o-rings. For example, the at least two o-rings may be integrated with the molding or casing and may be formed from overmolding or insert molding. Alternatively, the at least two o-rings may be separated from the molding or casing and may sit within glands included on the molding or casing.

Figure 1:
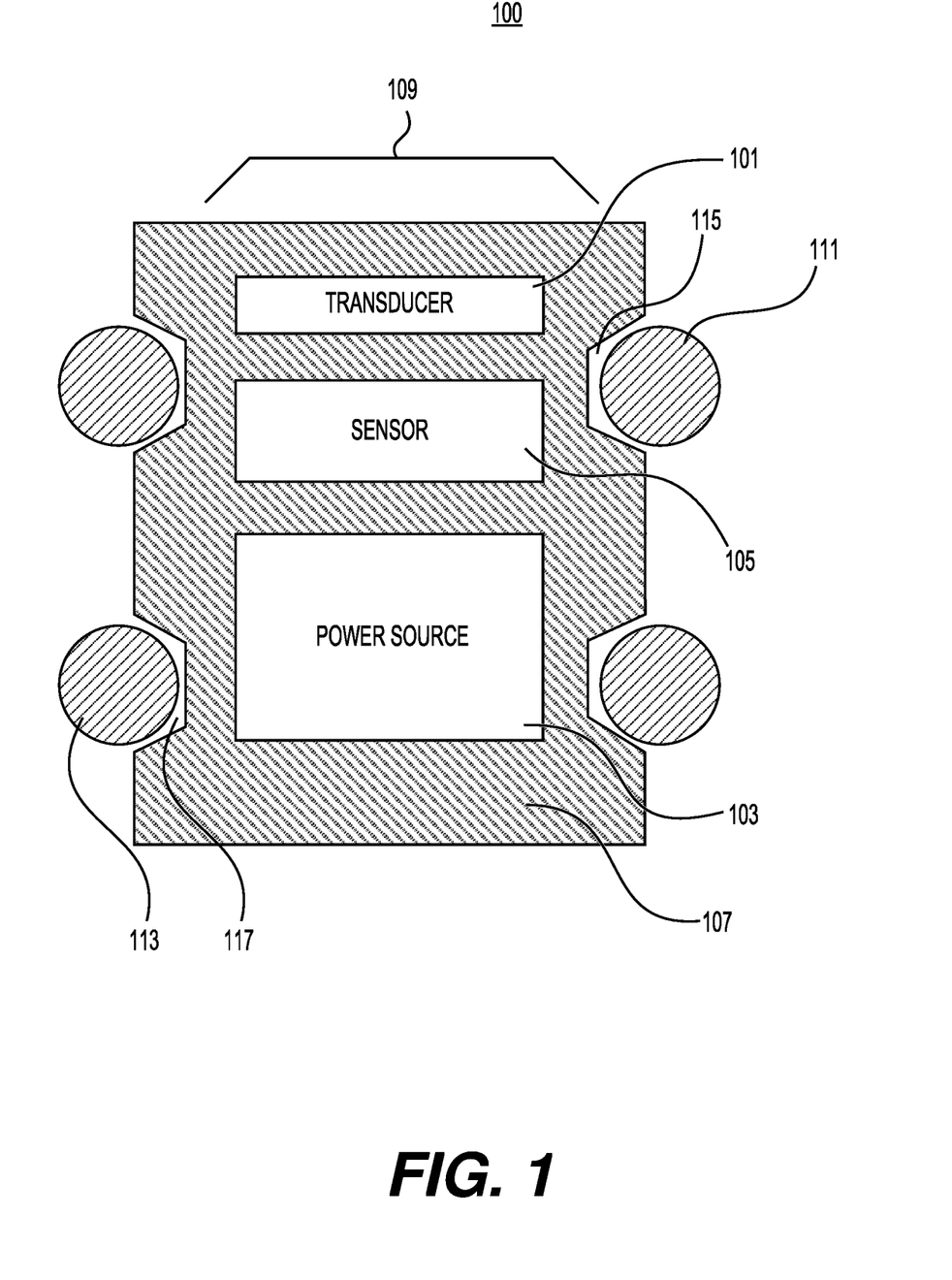
FIG. 1 is a cross-sectional schematic representation of an exemplary rigid sensor stopper, according to embodiments of the present disclosure.

FIG. 1 is a cross-sectional schematic representation of exemplary rigid sensor stopper 100. Stopper 100 may include transducer 101, power source 103, and sensor 105. Transducer 101, power source 103, and sensor 105 may be connected via one or more electrical connections. Stopper 100 may further include other electronic components, e.g., a microcontroller, an amplifier, an analog-to-digital converter, etc., operably connected to transducer 101, power source 103, and sensor 105. Stopper 100 may also include one or more telemeters, e.g., a radio transmitter, an antenna, etc., operably connected to transducer 101, power source 103, and sensor 105.

In some embodiments, transducer 101 may include an ultrasonic transducer. For example, transducer 101 may include a PZT transducer. In some embodiments, power source 103 may comprise a DC power source and include a battery, a capacitor, etc. In other embodiments, power source 103 may comprise an AC power source. In some embodiments, sensor 105 may include, for example, an acoustic transceiver, a photodiode, an encoder, a hall effect sensor, etc.

As depicted in FIG. 1, stopper 100 may include rigid molding 107. For example, rigid molding 107 may be formed from overmolding and may surround transducer 101, power source 103, sensor 105, and any other electronics components and telemeters. In other embodiments, rigid molding 107 may be formed from insert molding and may surround transducer 101, power source 103, sensor 105, and any other electronics components and telemeters.

Rigid molding 107, transducer 101, power source 103, sensor 105, and any other electronics components and telemeters may comprise sensor cone 109. Sensor cone 109 may comprise a cone, cylinder, or other conical or oblong shape. FIG. 1 therefore depicts a cross-sectional plane of sensor cone 109.

As depicted in FIG. 1, stopper 100 may further include one or more elastomeric seals, e.g., o-rings 111 and 113. For example, o-rings 111 and 113 may sit within glands, e.g., glands 115 and 117, that may be included on rigid molding 107. Here gland recesses are trapezoidal, but in other embodiments gland recesses may be rectangular, semicircular, or the like.

In stopper 100, sensor 105 may activate due to an environmental change, for example, if the pressure on the stopper increases. In such arrangements, sensor 105 may use power source 103 to supply power to transducer 101. Power source 103 may drive transducer 101 at a resonance frequency in order to emit an ultrasonic signal. Transducer 101 emits ultrasonic waves along the length of a cartridge or syringe holding a fluid (e.g., insulin), the signals are reflected back towards transducer 101 from a dispensing end of the cartridge, and then the ultrasonic signals are received by transducer 101 (or other sensor/transducer). The time between emission and receipt of the ultrasonic signals may be used to calculate a time of flight. The time of flight data, or other data generated by transducer 101, may be sent (e.g., by telemetry) to a detector, (for example, a smart phone, a keychain, or other device to display the data to a user) after the signal from transducer 101 is processed (e.g., the volume of fluid in the injection device is calculated with a controller or processor).

Figure 2A:
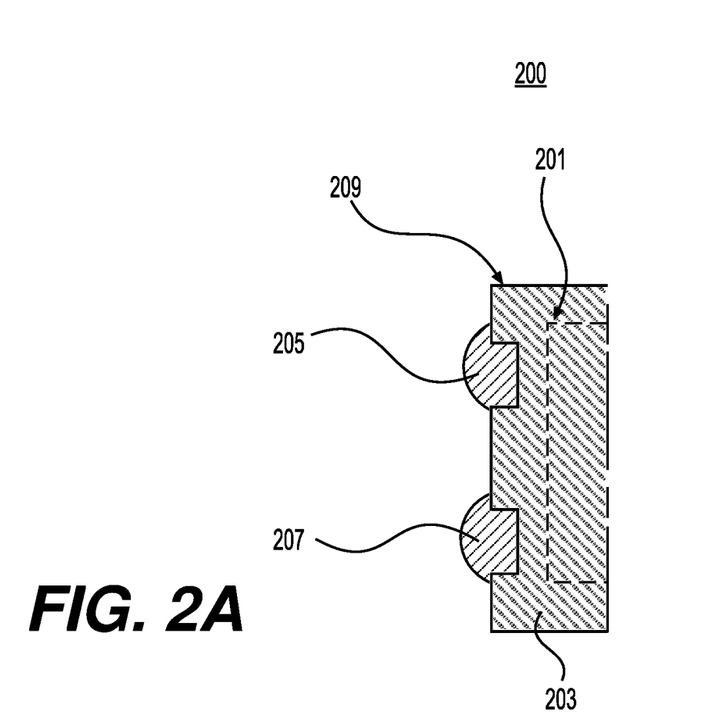
FIG. 2A is a cross-sectional schematic representation of another exemplary rigid sensor stopper, according to embodiments of the present disclosure.

FIG. 2A is a cross-sectional schematic representation of exemplary rigid sensor stopper 200. Stopper 200 may include a plurality of electronics 201. For example, the plurality of electronics may include a transducer, a power source, a sensor, a microcontroller, an amplifier, an analog-to-digital converter, a radio transmitter, an antenna, etc., or any combination thereof. The plurality of electronics 201 may be operably connected to each other.

As depicted in FIG. 2A, stopper 200 may include rigid molding 203. For example, rigid molding 203 may be formed from overmolding and may surround the plurality of electronics 201. In other embodiments, rigid molding 203 may be formed from insert molding and may surround the plurality of electronics 201.

As depicted in FIG. 2A, stopper 200 may further include one or more elastomeric seals, e.g., seals 205 and 207. In some embodiments, seals 205 and 207 may be formed from overmolding and may be integrated with rigid molding 203. In other embodiments, seals 205 and 207 may be formed from insert molding and may be integrated with rigid molding 203. Seals 205 and 207 may also be formed separately and bonded.

Rigid molding 203, the plurality of electronics 201, and seals 205 and 207 may comprise sensor cone 209. Sensor cone 209 may comprise a cone, cylinder, or other conical or oblong shape. FIG. 2A therefore depicts a cross-sectional plane of sensor cone 209.

In stopper 200, a sensor included in the plurality of electronics 201 may activate due to an environmental change, for example, if the pressure on the stopper increases, temperature changes, ambient light changes, electrical conductivity of solution changes, capacitance or resistance changes, or the stopper is exposed to an RF field (e.g., RFID, NFC, etc.). In such arrangements, the sensor may use a power source included in the plurality of electronics 201 to supply power to a transducer included in the plurality of electronics 201. The power source may drive a transmitter or telemeter (e.g., RF, Bluetooth or the like) in order to transmit a data signal to an external device. The data signal from the transmitter may be received by a detector included in, for example, a smart phone, a keychain, or other device adapted to receive data signals from the transmitter and display data to the user (e.g., on a screen).

Figure 2B:
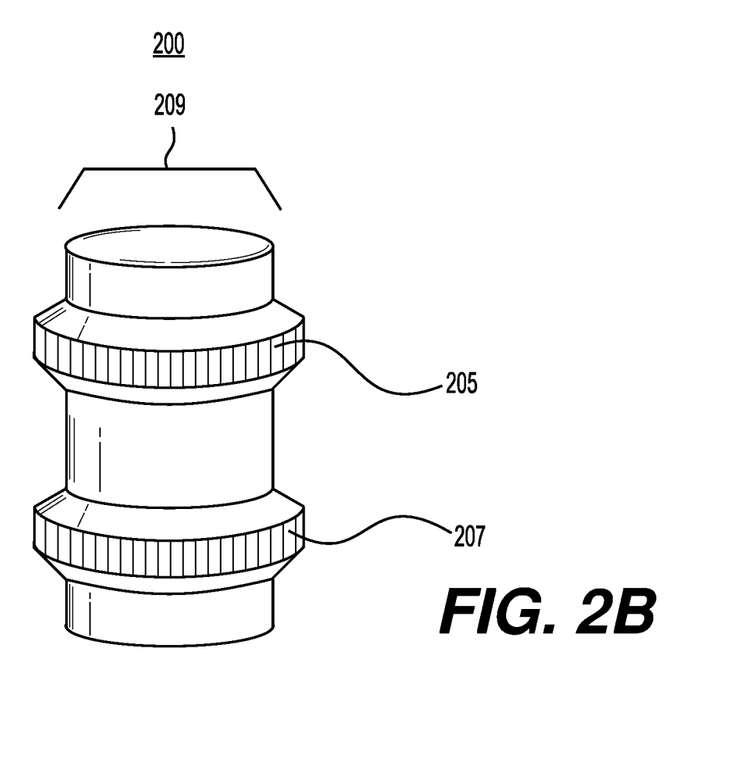
FIG. 2B is a front view of the exemplary rigid sensor stopper of FIG. 2A, according to embodiments of the present disclosure.

FIG. 2B is a front view of exemplary rigid sensor stopper 200 of FIG. 2A. FIG. 2B shows the overall shape of sensor cone 209 of stopper 200.

Figure 3:
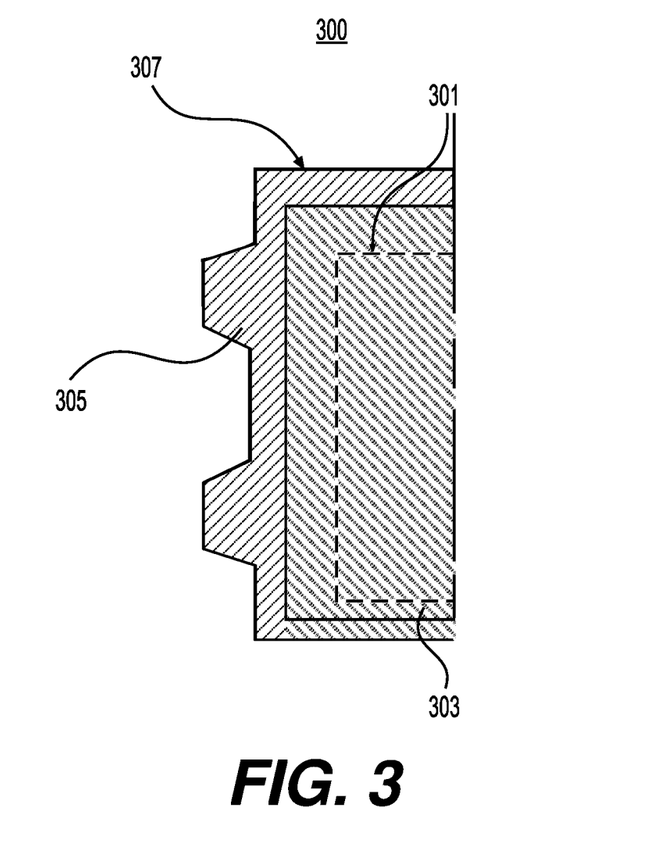
FIG. 3 is a cross-sectional schematic representation of another exemplary rigid sensor stopper, according to embodiments of the present disclosure.

FIG. 3 is a cross-sectional schematic representation of exemplary rigid sensor stopper 300. Stopper 300 may include a plurality of electronics 301. For example, the plurality of electronics may include a transducer, a power source, a sensor, a microcontroller, an amplifier, an analog-to-digital converter, a radio transmitter, an antenna, etc., or any combination thereof. The plurality of electronics 301 may be operably connected to each other.

As depicted in FIG. 3, stopper 300 may include rigid molding 303. For example, rigid molding 303 may be formed from overmolding and may surround the plurality of electronics 301. In other embodiments, rigid molding 303 may be formed from insert molding and may surround the plurality of electronics 301.

As depicted in FIG. 3, stopper 300 may further include an elastomeric seal, e.g., seal 305. In some embodiments, seal 305 may be formed from overmolding and may surround rigid molding 303. In other embodiments, seal 305 may be formed from insert molding and may surround rigid molding 303. In the depicted embodiment, seal 305 and the ridges, which are substantially trapezoidal, are one continuous piece of material (rather than using o-rings).

Rigid molding 303, the plurality of electronics 301, and seal 305 may comprise sensor cone 307. Sensor cone 307 may comprise a cone, cylinder, or other conical or oblong shape. FIG. 3 therefore depicts a cross-sectional plane of sensor cone 307.

In stopper 300, a sensor included in the plurality of electronics 301 may activate due to an environmental change, for example, if the pressure on the stopper increases. In such arrangements, the sensor may use a power source included in the plurality of electronics 301 to supply power to a transducer included in the plurality of electronics 301. The power source may drive the transducer at a resonance frequency in order to emit an ultrasonic signal. A data signal may be sent from a transmitter (also coupled to the power source) and may be received by a detector, for example, a smart phone, a keychain, or other device adapted to receive data signals and display data to the user.

Figure 4:
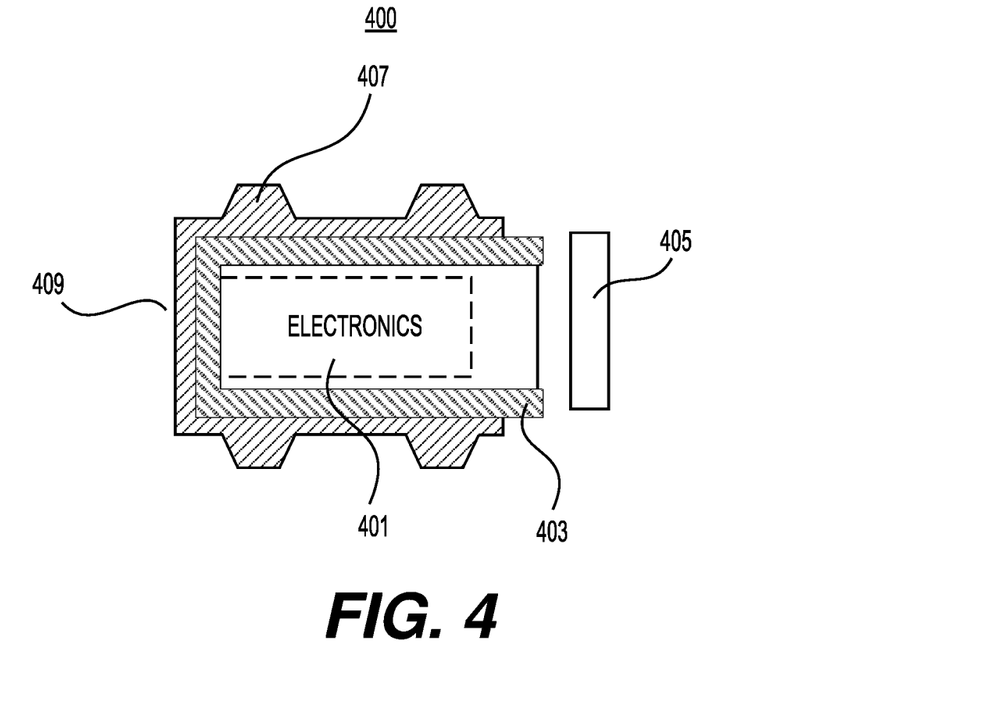
FIG. 4 is a cross-sectional schematic representation of another exemplary rigid sensor stopper, according to embodiments of the present disclosure.

FIG. 4 is a cross-sectional schematic representation of exemplary rigid sensor stopper 400. Stopper 400 may include a plurality of electronics 401. For example, the plurality of electronics may include a transducer, a power source, a sensor, a microcontroller, an amplifier, an analog-to-digital converter, a radio transmitter, an antenna, etc., or any combination thereof. The plurality of electronics 401 may be operably connected to each other.

As depicted in FIG. 4, stopper 400 may include rigid casing 403. For example, rigid casing 403 may surround the plurality of electronics 401. In some embodiments, rigid casing 403 may be formed from injection molding. In other embodiments, rigid casing 403 may be formed from machining. In still other embodiments, rigid casing 403 may be formed from forged casing.

Stopper 400 may further include potting and/or backfill (see infra discussion of phase change material and FIG. 7) within rigid casing 403. Advantageously, this may remove dead space within casing 403 and secure the plurality of electronics 401. Stopper 400 may further include a getter (e.g., a substance used to remove residual gas/liquid) within rigid casing 403. Advantageously, this may absorb moisture within casing 403 that could damage the plurality of electronics 401. Stopper 400 may further include soundboard (e.g., a thin sheet of material to improve wave production) within rigid casing 403. Advantageously, this may improve the range of a transducer included in the plurality of electronics 401.

Rigid casing 403 may be sealed using cap 405. For example, cap 405 may seal rigid casing 403 after the plurality of electronics 401 have been inserted therein. In some embodiments, an adhesive may attach cap 405 to rigid casing 403. In other embodiments, cap 405 may be welded onto rigid casing 403. In some embodiments, cap 405 may be secured by an interference fit, or include snap (e.g., snaps on the cap or on the rigid casing) fasteners, or may be secured by additional fasteners.

As depicted in FIG. 4, stopper 400 may further include an elastomeric seal, e.g., seal 407. In some embodiments, seal 407 may be formed from overmolding and may surround rigid casing 403. In other embodiments, seal 407 may be formed from insert molding and may surround rigid casing 403.

Rigid casing 403, the plurality of electronics 401, and seal 407 may comprise sensor cone 409. Sensor cone 409 may comprise a cone, cylinder, or other conical or oblong shape. FIG. 4 therefore depicts a cross-sectional plane of sensor cone 409.

In stopper 400, a sensor included in the plurality of electronics 401 may activate due to an environmental change, for example, if the pressure on the stopper increases. In such arrangements, the sensor may use a power source included in the plurality of electronics 401 to supply power to a transducer included in the plurality of electronics 401. The power source may drive the transducer at a resonance frequency in order to emit an ultrasonic signal. A transmitter may send a data signal that is received by a detector, for example, a smart phone, a keychain, or other device adapted to receive signals from the transmitter and display data (e.g., the volume of the cartridge or syringe) to the user.

Figure 5:
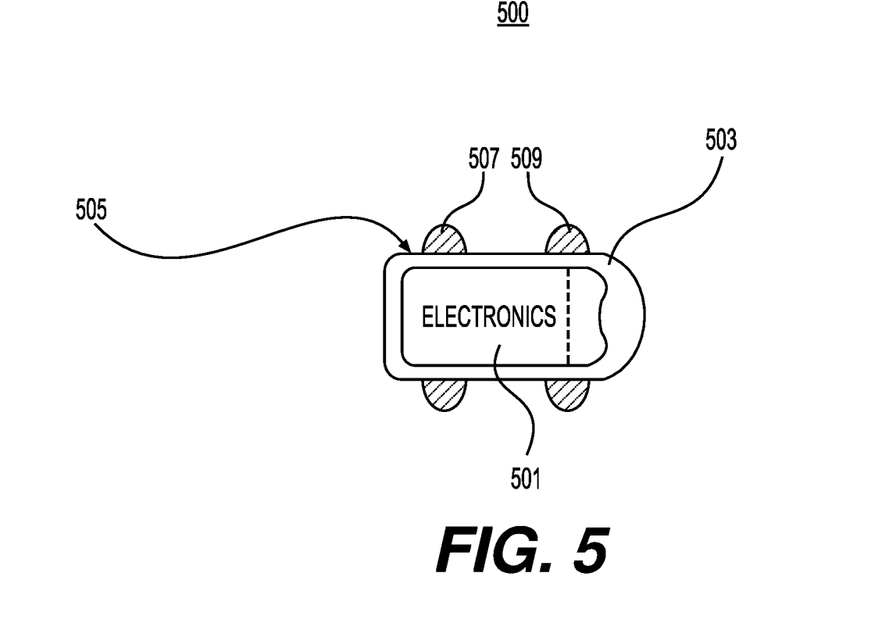
FIG. 5 is a cross-sectional schematic representation of another exemplary rigid sensor stopper, according to embodiments of the present disclosure.

FIG. 5 is a cross-sectional schematic representation of exemplary rigid sensor stopper 500. Stopper 500 may include a plurality of electronics 501. For example, the plurality of electronics may include a transducer, a power source, a sensor, a microcontroller, an amplifier, an analog-to-digital converter, a radio transmitter, an antenna, etc., or any combination thereof. The plurality of electronics 501 may be operably connected to each other.

As depicted in FIG. 5, stopper 500 may include rigid casing 503. For example, rigid casing 503 may surround the plurality of electronics 501. In certain aspects, rigid casing 503 may include glass. In some embodiments, rigid casing 503 may be sealed with flame sealing after the plurality of electronics 501 have been inserted therein. In other embodiments, rigid casing 503 may be sealed with laser sealing after the plurality of electronics 501 have been inserted therein.

Stopper 500 may further include potting and/or backfill within rigid casing 503. Advantageously, this may remove dead space within casing 503 and secure the plurality of electronics 501. Stopper 500 may further include a getter within rigid casing 503. Advantageously, this may absorb moisture within casing 503 that could damage the plurality of electronics 501. Stopper 500 may further include soundboard within rigid casing 503. Advantageously, this may improve the range of the transducer.

Rigid casing 503 and the plurality of electronics 501 may comprise sensor cone 505. Sensor cone 505 may comprise a cone, cylinder, or other conical or oblong shape. FIG. 5 therefore depicts a cross-sectional plane of sensor cone 505.

As depicted in FIG. 5, stopper 500 may further include one or more elastomeric seals, e.g., o-rings 507 and 509. For example, o-rings 507 and 509 may sit within glands (e.g., recesses) that may be included on rigid casing 503.

In stopper 500, a sensor included in the plurality of electronics 501 may activate due to an environmental change, for example, if the pressure on the stopper increases. In such arrangements, the sensor may use a power source included in the plurality of electronics 501 to supply power to a transducer included in the plurality of electronics 501. The power source may drive the transducer at a resonance frequency to emit the ultrasonic signals. A transmitter may send data signals to a detector, for example, a smart phone, a keychain, or other device adapted to receive signals from the transmitter and display data to the user (e.g., in the form of a graph, table, or the like).

Figure 6:
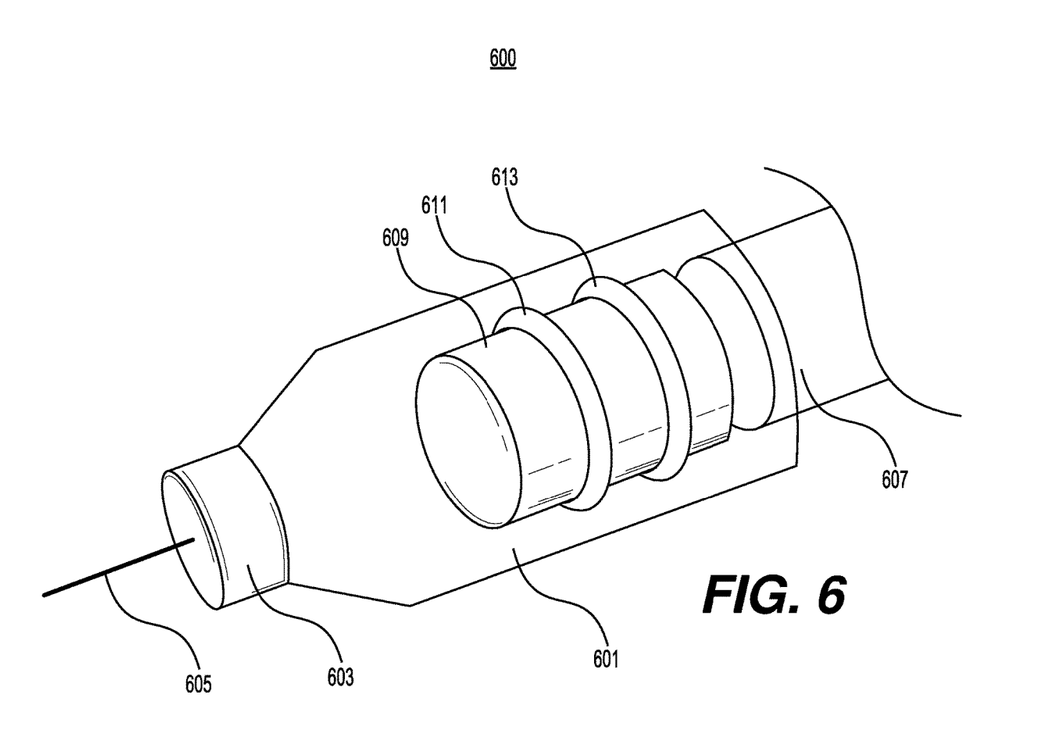
FIG. 6 illustrates an application of the disclosed rigid sensor stopper in a syringe.

FIG. 6 is a schematic representation of an application of a rigid sensor stopper (e.g., 100, 200, 300, 400, 500, or any combination thereof) in a syringe 600. In the example of FIG. 6, syringe 600 may include a barrel 601, a tip 603, a needle 605, and a dispensing mechanism 607. The example of FIG. 6 may further include a rigid sensor stopper 609. Stopper 609 may comprise stopper 100, 200, 300, 400, 500, or any combination thereof, consistent with the present disclosure.

In syringe 600, depressing dispensing mechanism 607 causes medicine contained within barrel 601 to move towards tip 603 and through needle 605. One or more seals, e.g., seals 611 and 613, included in rigid sensor stopper 609 may form a seal with barrel 601 such that the medicine contained within barrel 601 is forced through the dispensing end and needle 605. A sensor included in rigid sensor stopper 609 may activate when dispensing mechanism 607 is depressed because, for example, stopper 609 will undergo an increase in pressure. The sensor may use a power source included in rigid sensor stopper 609 to supply power to a transducer included in rigid sensor stopper 609. The power source may drive the transducer at a resonance frequency in order to emit an ultrasonic signal. A transmitter may emit a data signal which is received by a detector, for example, a smart phone, a keychain, or other device adapted to receive data signals from the transmitter and display data to the user.

In syringe 600, further depressing dispensing mechanism 607 causes rigid sensor stopper 609 to enter tip 603. A sensor included in rigid sensor stopper 609 may activate when entering tip 603 because, for example, stopper 609 will undergo an decrease in pressure.

Figure 7:
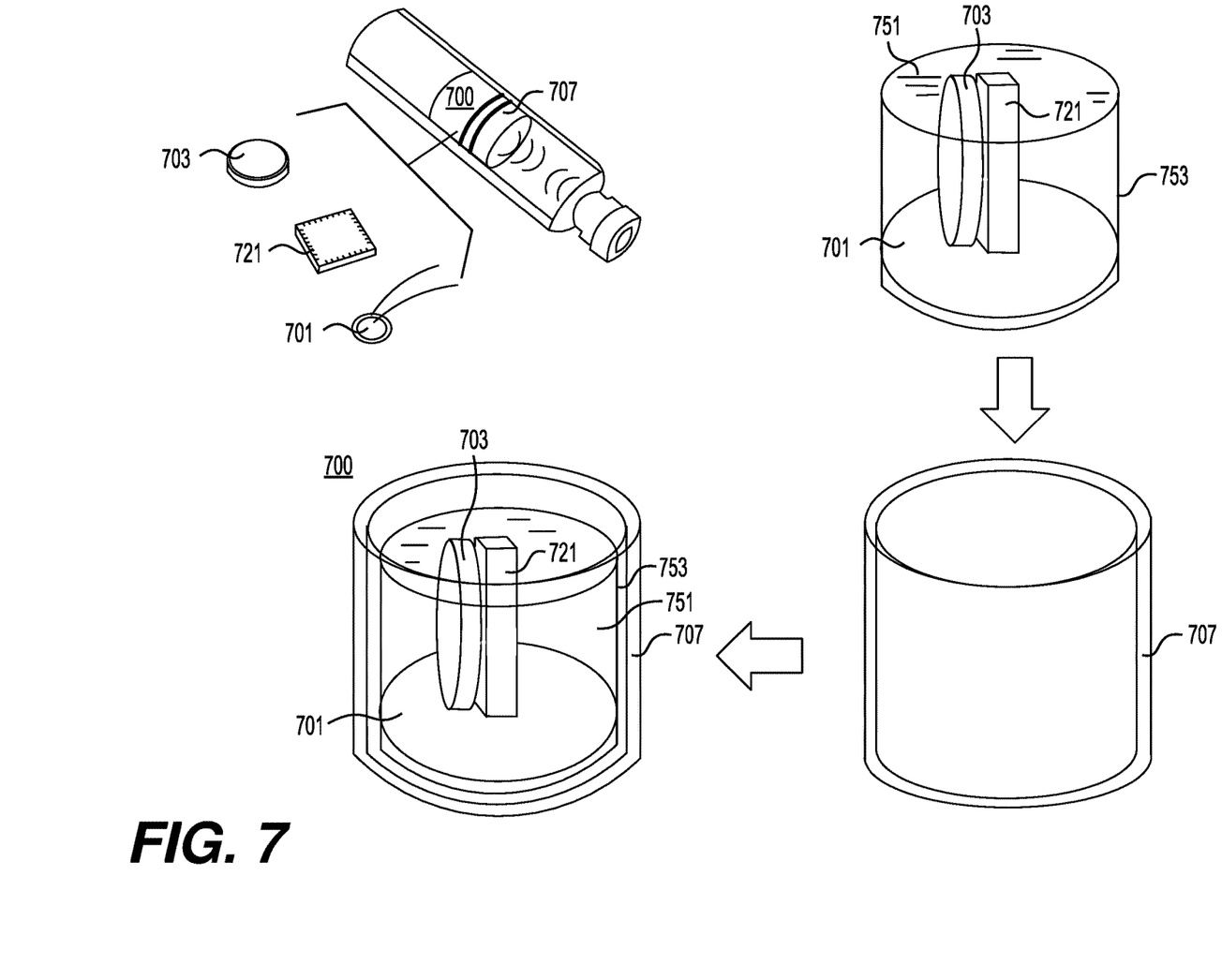
FIG. 7 illustrates a sensor stopper with a thermal protection barrier, in accordance with embodiments of the present disclosure.

FIG. 7 shows a sensor stopper 700 with a thermal protection barrier 751. Sensor stopper 700 includes transducer 701, power source 703 (e.g., a battery, capacitor), microcontroller 721 (e.g., processor), molding 707, can/housing 753, and phase change material 751. It is appreciated that the components depicted here are all compatible with the previously described stoppers (e.g., 100, 200, 300, 400, 500, or any combination thereof).

Aqueous based batteries, such as silver oxide, alkaline zinc, etc. may suffer from damage when exposed to high temperatures due to high cell internal pressure (boiling of electrolyte), faster corrosion reaction/side reaction at high temperatures, compromised sealing due to softening of the sealing element, etc. Often, medical devices integrated with batteries need to go through a sterilization process in which batteries can be exposed to 125° C. for ~30 mins. Here, phase change material 751 is used to prevent the negative effects of high temperature exposure.

In the depicted embodiment, stopper 700 includes transducer 701 which is coupled to emit ultrasonic signals (e.g., curved lines in the cartridge traveling away from stopper 700) through a fluid in the drug delivery device, along a length of the device, when the stopper is positioned in the drug delivery device (e.g., the cartridge of an insulin pen or the body of a syringe). As shown, the ultrasonic signals are reflected back toward the stopper by a dispensing end of the cartridge (see e.g., curved lines traveling towards stopper 700). As shown, the dispensing end of stopper 700 is the narrowing, or neck, region of the cartridge which provides a flat surface for the ultrasonic signals to be reflected off of. Power source 703 is disposed in stopper 700, and coupled to transducer 701 to supply power to transducer 701. Power source 703 is disposed within phase change material 751 (depicted as parallel lines filling can 753), and phase-change material 751 has a chemical structure to change phase at a temperature lower than a degradation temperature of the battery (e.g., the temperature at which the battery is at least one of physically damaged, has a permanent reduction in specific energy, or has a permanent reduction in specific power).

Microcontroller 721 is coupled to transducer 701 and power source 703. Controller 721 includes logic that, when executed by controller 721, causes stopper 700 to perform a variety of operations. For example, controller 721 may calculate a time of flight for the ultrasonic signals, a position of the plunger head, a volume of the cartridge, instruct the transmitter to send a data signal, or the like. In the depicted embodiment, both battery 703 and microcontroller 721 are placed in can 753 (e.g., a plastic or metal enclosure) and oriented orthogonal to transducer 701.

In some embodiments, controller 721 may calculate a time of flight for the ultrasonic signals to travel from transducer 701 and return to stopper 700 (e.g., be received by transducer 701 or another transducer in stopper 700). The time of flight may be used to calculate the position of stopper 700 in the cartridge. The position of stopper 700 may then be used to calculate a volume of fluid, medication, or insulin left in the cartridge.

As shown, one way to protect the electronics in sensor stopper 700 is to surround them with, or immerse them in, a material 751 (e.g., hydrocarbons like wax, or other low molecular weight polymer) that undergoes a phase change (e.g., solid to liquid, liquid to gas, or change between different crystal structures) at, or around, the sterilization temperature. This is because when materials change phase, the material's temperature remains constant. The heat supplied during a phase change is called latent heat (e.g., of fusion or vaporization). The energy supplied by the heat is used to change the molecular/atomic organization of the material rather than cause a temperature increase. When the phase change is completed, further transfer of heat will result in the temperature increasing. Here, a material may be selected to undergo a phase change at or around the sterilization temperature, to prevent the temperature of the microelectronics, including battery 703, from getting too hot.

In some embodiments, in addition to surrounding battery 703 with a phase change material, a specially designed high-temperature battery 703 (e.g., Li/CF$_X$ or Li/SOCl$_2$) may be employed. Battery 703 may include high boiling point solvent and a special sealing design. For example the battery could be FDK ML614 and have 3.4 mAh, and a max current of 15 uA. Similarly, battery 703 may be a reflowable ML614R which has 2.5 mAh and 5 uA discharge current. In a different embodiment, the battery may be a low-cost battery, and phase change material 751 provides adequate protection for sterilization.

In specific embodiments, electronics may be embedded (e.g., the phase change material may be in liquid form and poured into can 753 around the electronics) in phase change material 751 that has a phase change temperature lower than 150° C., 140° C., 130° C., 120° C., 110° C., or 100° C. The overmolded electronics may be loaded into a premolded butyl rubber cupped stopper 707 to form stopper 700. During the sterilization process, phase change material 751 will melt but will maintain its phase change temperature for some time without heating up battery 703. Depending stages of the sterilization process, phase change material 751 can be a mixture of phase change materials with different melting temperatures to manage the heat from the sterilization process. Put another way, phase change material 751 may include a plurality of materials, and each material in the plurality of materials has a different phase transition temperature.

Figure 8:
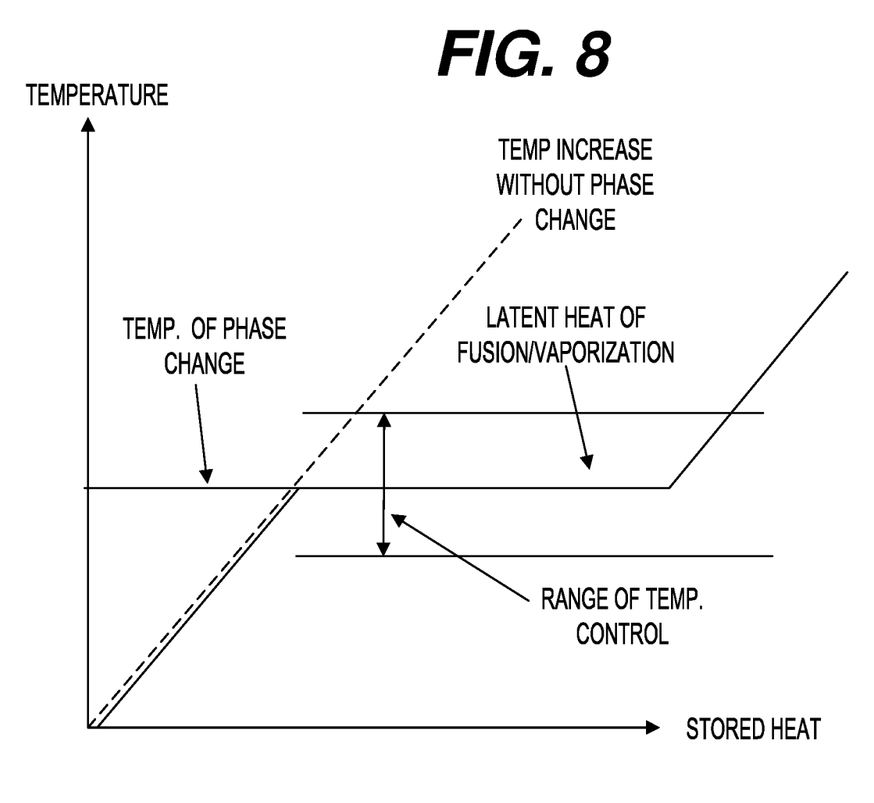
FIG. 8 depicts a graph showing how the latent heat of fusion or vaporization can be used to control the temperature of electronics, in accordance an embodiment of the present disclosure.

FIG. 8 depicts a graph showing how the latent heat of fusion or vaporization can be used to control the temperature of power source and other sensitive electronics. As shown, at the latent heat of fusion/vaporization, the temperature of the material is constant. This provides protection for the microelectronic devices that may be contained within. One of ordinary skill in the art having the benefit of the present disclosure will appreciate that this phase change technique to protect electronics during sterilization, may be used with other devices (e.g., continuous glucose monitors, wearable insulin delivery systems, other patch-like health monitoring devices, and even implantable medical devices) and not just the stopper described herein.

Figure 9A:
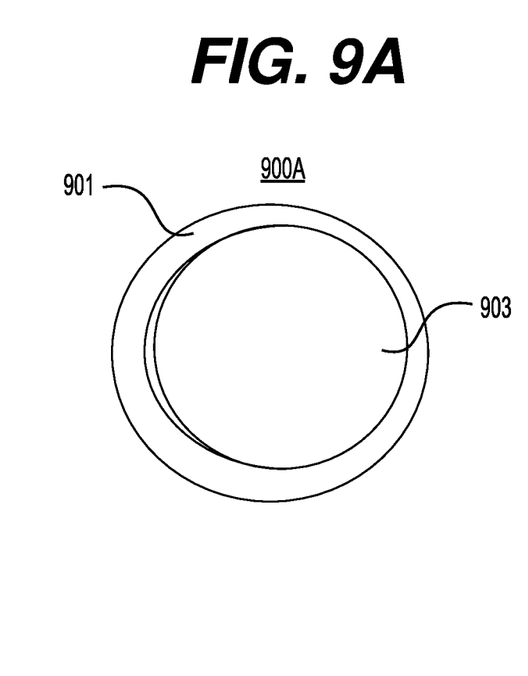
FIGS. 9A and 9B depict two examples of wearable devices that may utilize a phase-change-material-surrounded power source, in accordance with embodiments of the present disclosure.
Figure 9B:
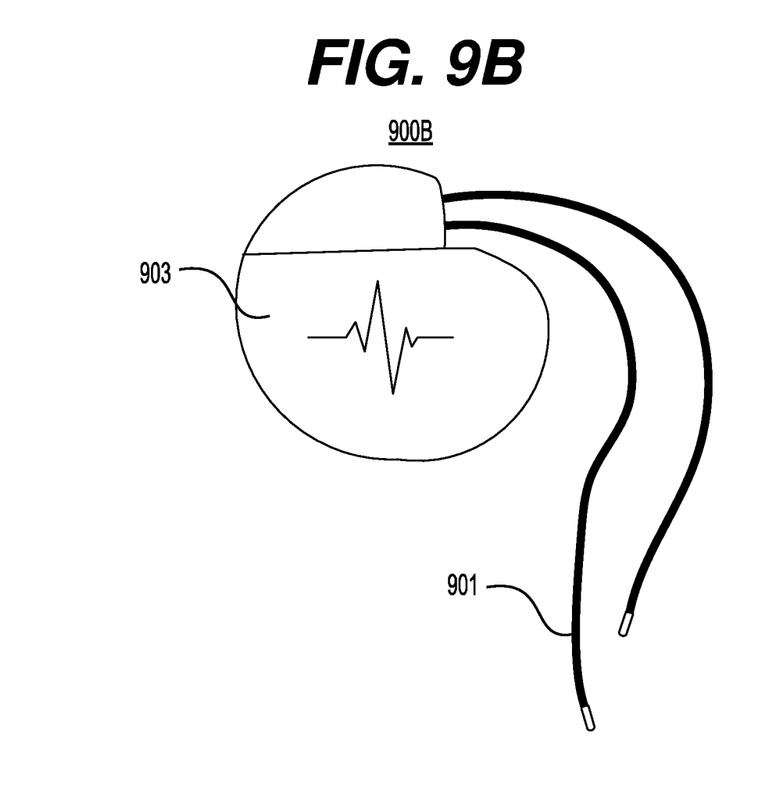

FIGS. 9A and 9B depict two examples of wearable devices that may utilize the phase-change-material-surrounded power source discussed above, in accordance with the teachings of the present disclosure. FIG. 9A depicts a continuous glucose monitor 900A (e.g., an adhesive patch) that may include a controller, glucose sensor (e.g., chemical sensor array), adhesive layer 903, and power source (e.g., battery) surrounded by a phase change material. All of these components may be disposed in housing 903. In some embodiments, the glucose monitor 900A may double as an insulin delivery system or. Moreover, glucose monitoring patch 900A may also include other sensors to detect physical attributes such as heart rate, blood pressure, or the like.

Similarly FIG. 9B shows an example pacemaker 900B which may include a power source surrounded by a phase change material as well as other electronic components (e.g., microcontroller, electrodes 901, etc.). Like the other embodiments, the phase change material may be disposed around the power source (and other electronics described herein) so during sterilization, the power source is not damaged.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A rigid sensor stopper adapted for a drug delivery device, comprising:
   a transducer;
   a power source coupled to the transducer;

a rigid casing, wherein the transducer and the power source are disposed within the rigid casing;

at least one seal disposed around the rigid casing, the at least one seal comprising an elastomeric material; and a phase-change material disposed within the rigid casing and having a chemical structure to change phase at a temperature lower than a degradation temperature of the power source, wherein the power source is disposed within the phase change material.

2. The device of claim 1, wherein the at least one seal comprises at least two o-rings.

3. The device of claim 1, wherein the at least one seal comprises at least one of: an overmolding or an insert molding.

4. The device of claim 2, wherein the at least two o-rings are each distinct components and sit within glands on the rigid casing.

5. The device of claim 1, wherein the at least one seal coats the rigid casing.

6. The device of claim 5, wherein the at least one seal includes one or more ridges that encircle the rigid casing.

7. The device of claim 1, further comprising at least one of: a microcontroller, an amplifier, an analog-to-digital converter, a radio transmitter, or an antenna disposed within the rigid casing and coupled to the power source.

8. The rigid sensor stopper of claim 1, wherein the degradation temperature is a temperature at which the power source is at least one of physically damaged, has a permanent reduction in specific energy, or has a permanent reduction in specific power.

9. The rigid sensor stopper of claim 1, wherein the chemical structure of the phase-change material undergoes a solid-to-liquid transition or a solid-to-gas transition at the temperature lower than the degradation temperature of the power source, and wherein the phase change material is in contact with the power source.

10. The rigid sensor stopper of claim 9, wherein the phase-change material includes at least one of a polymer or a hydrocarbon.

11. The rigid sensor stopper of claim 1, wherein the phase change material includes a plurality of materials, and wherein each material in the plurality of materials has a different phase transition temperature.

12. The rigid sensor stopper of claim 1, wherein the power source includes at least one of a battery including silver oxide, alkaline zinc, Li, $CF_x$, or $SOCl_2$.

13. A rigid sensor stopper adapted for a drug delivery device, comprising:

a power source;

a transducer, wherein the transducer is configured to emit ultrasonic signals along a length of, and through a fluid in, a drug delivery device when the rigid sensor stopper is positioned in the drug delivery device, and wherein the power source is coupled to the transducer to supply power to the transducer;

a rigid casing, wherein the transducer and the power source are disposed within the rigid casing;

a seal disposed around the rigid casing, the seal comprising an elastomeric material; and a controller coupled to the transducer and the power source, wherein the controller includes logic that when executed by the controller causes the rigid sensor stopper to perform operations including:

calculating a time of flight for the ultrasonic signals to travel from the transducer and return to the rigid sensor stopper.

14. The rigid sensor stopper of claim 13, wherein the power source comprises a battery disposed within the rigid casing.

15. The rigid sensor stopper of claim 13, further comprising:

a phase-change material disposed within the rigid casing and having a chemical structure to change phase at a temperature lower than a degradation temperature of the power source, wherein the power source is disposed within the phase change material.

16. The rigid sensor stopper of claim 13, wherein the seal comprises at least one o-ring.

17. A sensor stopper adapted for a drug delivery device, comprising:

a transducer;

a controller;

a battery coupled to the transducer and the controller;

a housing, wherein the transducer, the battery, and the controller are disposed within the housing;

an elastomeric material disposed around the housing; and a phase-change material disposed within the housing and having a chemical structure to change phase at a temperature lower than a degradation temperature of the power source, wherein the battery and the controller are disposed within the phase change material.

* * * * *